United States Patent [19]

Merger et al.

[11] 4,315,869
[45] Feb. 16, 1982

[54] PREPARATION OF α,β-UNSATURATED NITRILES

[75] Inventors: Franz Merger, Frankenthal; Hans-Martin Hutmacher, Ludwigshafen; Helmut Hagen, Frankenthal, all of Fed. Rep. of Germany

[73] Assignee: BASF Aktiengesellschaft, Fed. Rep. of Germany

[21] Appl. No.: 143,446

[22] Filed: Apr. 24, 1980

[30] Foreign Application Priority Data

May 16, 1979 [DE] Fed. Rep. of Germany ... 2919630

[51] Int. Cl.³ .............................................. C07C 120/10
[52] U.S. Cl. ................................. 260/465.2; 546/246; 260/465 B; 260/464
[58] Field of Search ............... 260/465.2, 465 B, 464; 546/246

[56] References Cited

U.S. PATENT DOCUMENTS 3,256,311 6/1966 Becke et al. .................... 260/464
3,514,478 5/1970 Becke et al. .................... 260/465 B

FOREIGN PATENT DOCUMENTS 482943 9/1929 Fed. Rep. of Germany ... 260/465 B
1068241 11/1959 Fed. Rep. of Germany ... 260/465 B
1127890 10/1962 Fed. Rep. of Germany .
2036503 2/1972 Fed. Rep. of Germany .
907067 10/1962 United Kingdom ............. 260/465.2

OTHER PUBLICATIONS

Eiden et al., Archiv. der Pharmazie, 299, (1966), pp. 493-498.
Houben-Weyl, Methoden der Organischen Chemie, vol. 4/2, pp. 209-218, 1955.
Ullmanns Encyklopädie der technischen Chemie, vol. 12, pp. 751-764, (1960).
Moffat, Journal of Physical Chemistry, 81, (1977), pp. 82-86.
Lenz, Synthesis, 1978, pp. 489-495.

*Primary Examiner*—Joseph Paul Brust
*Attorney, Agent, or Firm*—Keil & Witherspoon

[57] ABSTRACT

α,β-Unsaturated nitriles are prepared by reacting an aldehyde with formamide in the presence of an acid and the presence or absence of a non-aromatic solvent to give an N-alkenyl-formamide, which is then passed, in the gas phase, over a dehydration catalyst at an elevated temperature.

The nitriles obtainable by the process of the invention are valuable starting materials for the preparation of dyes, crop protection agents, plasticizers and drugs.

13 Claims, No Drawings

PREPARATION OF α,β-UNSATURATED NITRILES

The present invention relates to a process for the preparation of α,β-unsaturated nitriles by reacting an aldehyde with formamide in the presence of an acid and in the presence or absence of a non-aromatic solvent, to give an N-alkenylformamide, and passing the latter, in the gas phase, over a dehydration catalyst at an elevated temperature.

German Pat. No. 1,127,890 discloses that α,β-unsaturated nitriles may be prepared by catalytic dehydrogenation of saturated nitriles at 500°–580° C. In addition, German Published Application DAS No. 1,117,121 discloses that saturated nitriles may be prepared by reaction and rearrangement of N-formylated primary monoamino compounds over silica catalysts having a particular structure. In the Examples, reaction temperatures of 400°–540° C. are mentioned. In a different form of the process (German Laid-Open Application DOS No. 2,036,503), α,β-unsaturated nitriles are obtained via N-formylated allylamines, which can only be prepared with difficulty and within certain limitations, by elimination of water and isomerization at from 500° to 800° C.

Archiv der Pharmazie, 299 (1966), 493–498 discloses the reaction of formamide with diphenylacetaldehyde in the presence of an acidic catalyst to give N-(β,β-diphenylvinyl)-formamide by heating the mixture, with benzene as an azeotropic entraining agent, for 50 hours under a water separator. If the reaction is carried out with amyl alcohol as the entraining agent, 1,1,5,5-tetraphenyl-3-azapenta-1,4-diene is obtained.

We have found that α,β-unsaturated nitriles of the formula

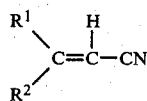
I where $R^1$ and $R^2$ may be identical or different and each is an aliphatic, cycloaliphatic, araliphatic, aromatic or heterocyclic radical, and $R^1$ and $R^2$ together with the adjacent carbon may also be members of a ring, are obtained in an advantageous manner by reacting aldehydes with acid amides in the presence of acidic catalysts and solvents, if, in a first step, an aldehyde of the formula

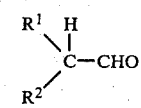
II where $R^1$ and $R^2$ have the above meanings, is reacted with formamide in the presence of a catalytic amount of an inorganic acid, sulfonic acid and/or halogen-substituted aliphatic carboxylic acid in the absence of an added solvent or in the presence of an organic nonaromatic solvent which is inert under the reaction conditions, after which, in a second step, the resulting N-alkenylformamide of the formula

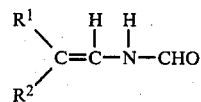
III where $R^1$ and $R^2$ have the above meanings, is passed, in the gas phase, over a dehydration catalyst at from 250°–700° C.

Where isobutyraldehyde is used, the reaction may be represented by the following equations:

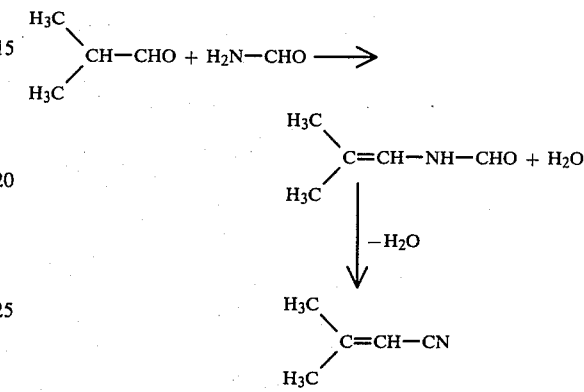

Compared to the conventional processes, the process according to the invention starts from readily obtainable starting materials and gives α,β-unsaturated nitriles more simply and more economically, and in better yield and higher purity. Compared to the publication in Archiv der Pharmazie, the reaction times are, surprisingly, in general substantially lower. All these advantageous characteristics are surprising in view of the prior art. Thus, it was not to be expected that a rearrangement of the intermediate isonitrile group to the nitrile group would occur, since the double bond is in the α,β-position and not in the β,γ-position of the molecule. In view of the article in Archiv der Pharmazie (loc. cit) it would have been expected that the reaction conditions according to the invention, using non-aromatic solvents, would lead to the formation of azepentadiene derivatives or at least to the formation of heterogeneous mixtures of different condensation products of the starting materials.

The starting materials II can be reacted with formamide in stoichiometric amounts or using an excess of either component relative to the other; preferably, the reaction is carried out with from 0.75 to 4, advantageously from 0.76 to 2, especially from 0.9 to 1.5, moles of starting material II per mole of formamide. Preferred starting materials II and accordingly preferred end products I are those where $R^1$ and $R^2$ are identical or different and each is alkyl of 1 to 7 carbon atoms, cycloalkyl of 5 to 7 carbon atoms, aralkyl or alkylaryl of 7 to 12 carbon atoms, phenyl or a 5-membered or 6-membered heterocyclic radical which may contain one or 2 nitrogen atoms and/or one oxygen atom, or $R^1$ and $R^2$ together with the adjacent carbon are members of a 5-membered or 6-membered alicyclic ring. The above radicals and rings may in addition be substituted by groups which are inert under the reaction conditions, for example alkyl or alkoxy, each of 1 to 4 carbon atoms.

Examples of suitable aldehydes for use as starting materials II are acetaldehydes disubstituted in the α-position by methyl, ethyl, propyl, isopropyl, butyl, isobutyl, sec.-butyl, tert.-butyl, cyclopentyl, cyclohexyl, benzyl, phenyl, o-tolyl, m-tolyl, p-tolyl, o-methoxyphenyl, m-methoxyphenyl, p-methoxyphenyl, pentyl, hexyl, heptyl or piperidin-2-yl, the substituents being identical or different, cyclohexylaldehyde and cyclopentyladehyde; preferred aldehydes are isobutyraldehyde, 2-methylbutanal, 2-methylpentanal, 2-ethylhexanal and 2-phenylpropanal.

The reaction constituting the first step is preferably carried out at from 40° to 150° C., advantageously at from 60° to 120° C., under atmospheric or superatmospheric pressure, continuously or batchwise. In general, the temperature and pressure conditions are chosen so that the reaction takes place in the liquid phase. Advantageously, from 0.5 to 25, more particularly from 1 to 18, preferablly from 1 to 8, hours are allowed for this first step.

The reaction is carried out in the presence of a catalytic amount of an acid, advantageously using from 0.1 to 15, in particular from 0.5 to 10, preferably from 0.5 to 5, equivalents of acid per mole of formamide. Instead of using monobasic acids, equivalent amounts of polybasic acids or of compounds which form such acids under the reaction conditions may be employed. Examples of acids which have proved suitable for use, as such or as their ammonium salts, are inorganic acids, eg. hydrogen chloride, hydrogen bromide, perchloric acid, sulfuric acid, phosphoric acid and nitric acid; sulfonic acids eg. benzenesulfonic acid and p-toluenesulfonic acid; boron-containing acids, eg. boric acid and fluoboric acid; halogen-substituted aliphatic carboxylic acids, eg. chloroacetic acid, dichloroacetic acid, trichloroacetic acid, monobromoacetic acid and α- or β-chloropropionic acid, and mixtures of the above. The acids may be used undiluted, as mixtures with one another and/or as mixtures with a solvent (in particular water). Preferred acids are sulfuric acid, phosphoric acid, p-toluenesulfonic acid, monochloroacetic acid, dichloroacetic acid and trichloroacetic acid. The reaction in stage 1 is advantageously carried out at a pH of from 1 to 6.9, preferably from 2 to 6.

The reaction may advantageously be carried out without an added solvent, in which case the starting mixture or reaction mixture serves as the medium (ie. as the liquid phase). However, it may also be carried out in the presence of organic non-aromatic solvents which are inert under the reaction conditions. Examples of such solvents are halohydrocarbons, especially chlorohydrocarbons, eg. tetrachloroethylene, 1,1,2,2- and 1,1,1,2-tetrachloroethane, amyl chloride, cyclohexyl chloride, dichloropropane, methylene chloride, dichlorobutane, isopropyl bromide, n-propyl bromide, butyl bromide, chloroform, ethyl iodide, propyl iodide, carbon tetrachloride, 1,1,1- and 1,1,2-trichloroethane, trichloroethylene, pentachloroethane, 1,2-dichloroethane, 1,1-dichloroethane, n-propyl chloride, 1,2-cis-dichloroethylene, n-butyl chloride and 2-, 3- and iso-butyl chloride; ethers, eg. ethyl propyl ether, methyl tert.-butyl ether, n-butyl ethyl ether, di-n-butyl ether, diisobutyl ether, diisoamyl ether, diisopropyl ether, cyclohexyl methyl ether, diethyl ether, ethylene glycol dimethyl ether, tetrahydrofuran and dioxane; esters. eg. methyl acetate, n-propyl acetate, methyl propionate, butyl acetate, ethyl formate and ethyl acetate; nitrohydrocarbons, eg. nitromethane and nitroethane; nitriles, such as fatty acid nitriles of 2 to 4 carbon atoms, eg. acetonitrile, propionitrile, butyronitrile and isobutyronitrile; alkanols and cycloalkanols, eg. ethanol, methanol, n-butanol, isobutanol, tert.-butanol, glycol, glycerol, n-propanol, isopropanol, amyl alcohol, cyclohexanol, 2-methyl-4-pentanol, ethylene glycol monoethyl ether, 2-ethylhexanol, methylglycol, n-hexanol, isohexyl alcohol, isoheptyl alcohol, n-heptanol, ethylbutanol, nonyl alcohol, dodecyl alcohol, methylcyclohexanol and diacetone-alcohol, those of 3 to 8 carbon atoms being preferred; carbon disulfide, sulfoxides and sulfones, eg. dimethylsulfoxide, diethylsulfoxide, dimethylsulfone, diethylsulfone, methylethylsulfone and tetramethylenesulfone; aliphatic and cycloaliphatic hydrocarbons, eg. heptane, α-pinene, pinane and nonane, gasoline fractions boiling within a range of from 50° to 150° C., cyclohexane, methylcyclohexane, decalin, petroleum ether, hexane, naphtha, 2,2,4-trimethylpentane, 2,2,3-trimethylpentane, 2,3,3-trimethylpentane and octane; and mixtures of the above. Advantageously, the solvent is used in an amount of from 10 to 500 percent by weight, preferably from 20 to 200 percent by weight, based on starting material II.

The reaction constituting the first step may be carried out as follows: a mixture of starting material II, formamide and acid, with or without solvent, is kept at the reaction temperature for the duration of the reaction time. The reactants may all be added entirely at the beginning of the reaction, or may in part be added during the reaction. Advantageously, the water formed during the reaction is removed from the reaction mixture, for example by distillation under reduced pressure or, more advantageously, by azeotropic distillation. In the latter case, suitable entraining agents are, in the case of the reaction of low-boiling aldehydes, the aldehydes themselves or, in the case of higher-boiling aldehydes, some of the solvents referred to above which are inert under the reaction conditions, eg. cyclohexane. After completion of the reaction, the end product is isolated from the reaction mixture in a conventional manner, for example by distillation or crystallization.

The second step of the reaction is carried out in the gas phase at from 250° to 700° C., preferably from 350° to 500° C., under atmospheric, superatmospheric or, advantageously, reduced pressure, preferably at from 0.1 to 500 mbar, especially from 0.5 to 200 mbar, continuously or batchwise. Advantageously, carrier gases which are inert under the reaction conditions, for example nitrogen, may be used, suitable amounts being from 20 to 80 percent by weight, based on the amount by weight of starting material III. In tubular reactors, the reaction is preferably carried out under reduced pressure, and in fluidized bed reactors preferably under atmospheric pressure, using nitrogen as a carrier gas.

The dehydration catalyst is in general used in an amount of from 0.01 to 20, preferably from 0.1 to 10, percent by weight based on starting material III. If the reaction is carried out continuously, from 1 to 100, advantageously from 2 to 50, moles of starting material III per hour per liter of catalyst are employed as a rule. In general, acids, eg. mineral acids such as phosphoric acid and sulfuric acid, are not used as catalysts. Advantageously, neutral or acidic dehydration catalysts are employed. Advantageous catalysts to use are acid-activated bentonites, eg. Florida earth and fuller's earth, bauxite, clay, kaolin and bleaching earth; phosphoric acid esters; oxides of aluminum, silicon, thorium, zinc, tungsten and titanium, eg. δ-aluminum oxide, active aluminum oxide, silica gel, blue tungsten oxide, titanium white, anatase, titanium dioxide/active charcoal, aluminum oxide/basic copper carbonate, aluminum oxide/nickel carbonate, aluminum oxide/zinc sulfide and aluminum oxide/zinc oxide; aluminum hydroxides and aluminum oxide hydrates, eg. diaspore boehmite, bayerite A and B and hydrargillite; mixtures of the above oxides, eg. aluminum oxide mixed with copper oxide, zirconium oxide, tungsten oxide, chromium oxide, thorium oxide, cerium(IV) oxide, molybdenum(IV) oxide, nickel oxide, cobalt oxide; silicon oxide/magnesium oxide/tantalum(V) oxide, silicon oxide/magnesium oxide/chromium(III) oxide and silicate gel or silica gel/metal oxides of groups III to VII of the periodic table, eg. oxides of aluminum, titanium, vanadium, chromium, manganese and tantalum; chlorides, bromides, sulfates, bisulfates, pyrosulfates, phosphates, pyrophosphates and borates of lithium, sodium, potassium, copper, magnesium, zinc, boron, calcium and aluminum, eg. zinc sulfate, boron phosphate, sodium aluminum sulfate, potassium aluminum sulfate, disodium phosphate, neutral calcium phosphate, magnesium pyrophosphate, nickel phosphate, aluminum phosphate, sodium phosphate/graphite, aluminum phosphate/pumice or mixtures, eg. copper phosphate/lithium phosphate/iron phosphate, sodium phosphate/butylamine phosphate and copper(I) bromide/ammonium bromide. Regarding the preparation of dehydration catalysts, reference may be made to Houben-Weyl, Methoden der Organischen Chemie, Volume 4/2, pages 209–218, and to German Laid-Open Application DOS No. 2,036,503.

Advantageously, the second step is carried out without an additional organic solvent; if desired, however, the inert non-aromatic solvents referred to in connection with the first step, preferably the carboxylic acid nitriles mentioned, may be present, as well as aromatic hydrocarbons and aromatic carboxylic acid nitriles, eg. toluene, benzene, xylenes, benzonitrile, o-tolunitrile, p-tolunitrile, and ethylbenzonitrile. Any solvent is advantageously used in an amount of from 10 to 1,000 percent by weight, preferably from 20 to 500 percent by weight, based on starting material III.

The reaction may be carried out as follows: the starting material III is vaporized and then passed over the catalyst, heated to the reaction temperature, in a tubular reactor. A residence time of from 0.001 to 40, especially from 0.01 to 20, seconds in the reaction zone is advantageous. The end product is isolated from the reaction mixture, leaving the reactor, in a conventional manner, for example by fractional distillation. However, it is also possible to take samples from the reaction mixture, ascertain the conversion analytically, for example gaschromatographically, determining the ratio of end product I to starting material III, and convert the reaction mixture further directly, without isolating the end product, for example hydrogenate it to give the corresponding saturated nitrile or amine.

In a preferred embodiment of the process, the starting materials are reacted in a fluidized bed at the reaction temperature. The catalyst, or supported catalyst, can advantageously be maintained in the form of a fluidized bed by means of an inert gas, a mixture of starting material III and an inert gas, or the gaseous starting material III alone, under atmospheric pressure, superatmospheric pressure or, in particular, reduced pressure. Accordingly, either the total amount, or a part, of the starting material III may be introduced separately from the fluidizing gas into the fluidized bed reactor. The starting material III can also be kept in the liquid state in a heated stock vessel and be fed from there into a vaporizer upstream of the fluidized bed reactor. It is advantageous if a slight stream of nitrogen, advantageously from 100 to 1,000 parts by volume of nitrogen per hour per part by volume of catalyst, is passed through the vaporizer at the same time. The vaporized starting materials are passed, together with the stream of nitrogen, through the catalyst bed. The concentration of starting material III in the inert gas is advantageously from 0.1 to 50 percent by volume. The process according to the invention can be carried out in a single or sub-divided, open or closed fluidized bed system, with or without circulation of the fluidized solid. Concerning the reactors, method of operation, different embodiments and reaction conditions of the fluidized bed process, reference may be made to Ullmanns Encyklopädie der technischen Chemie, Volume 1, pages 916 et seq. The reaction mixture is worked up in the manner described above.

The nitriles I obtainable by the process of the invention are valuable starting materials for the preparation of dyes, crop protection agents, plasticizers and drugs. When hydrogenated over palladium catalysts, which are advantageously supported, for example on charcoal or SiO$_2$, they give saturated nitriles. Regarding the use of the products, reference may be made to the publications cited above and to Ullmanns Encyklopädie der technischen Chemie, Volume 12, pages 751–764.

In the Examples, parts are by weight and bear the same relation to parts by volume as that of the kilogram to the liter.

EXAMPLE 1

(a) (1st step). 1,440 parts of isobutyraldehyde, 900 parts of formamide and 240 parts of toluenesulfonic acid are introduced into a stirred apparatus equipped with a reflux condenser and water separator, and the mixture is refluxed for 15 hours whilst keeping the internal temperature during the reaction at about 110° C. by adding a further 245 parts of isobutyraldehyde in portions. 318 parts of water are separated off. On subsequent distillation of the reaction mixture under reduced pressure, 1,527 parts of N-(2-methylprop-1-enyl)-formamide, boiling point 78°–81° C./0.4 mbar, are obtained, corresponding to a yield of 77.1% of theory, based on formamide employed.

(b) (2nd step). 105 parts of N-(2-methylprop-1-enyl)-formamide per hour are fed from a stock vessel into a horizontal quartz vaporizer heated to 220° C., and the vapor, together with 37,600 parts by volume per hour of nitrogen, is passed through the fluidized bed reactor heated to 500° C. The fluidized bed reactor is a vertical electrically heated quartz tube, surmounting the vaporizer, closed at the bottom by a sealed-in quartz frit. The quartz tube is one third filled with 100 parts by volume of a silica gel catalyst (bulk density 420 g/l, specific water absorption 1.39 cm$^3$/g, particle size 0.1–0.3 mm). The residence time in the fluidized catalyst zone is 3.5 seconds. The height of the fluidized catalyst zone is 80 mm. The vapors leaving the reactor are condensed and subjected to fractional distillation. Per hour, 58 parts (67.5% of theory, based on N-(2-methyl-prop-1-enyl)-formamide employed) of 3,3-dimethylacrylonitrile, boiling point 80° C./153 mbar, are obtained. The conversion of N-(2-methyl-prop-1-enyl)-formamide employed is virtually quantitative. The yield remains constant even after 300 hours' operation.

EXAMPLE 2

The procedure described in Example 1 is followed, but in stage 1(b) the catalyst used in silica gel of particle size 0.1–0.3 mm and bulk density 540 g/l (specific water absorption 0.92 cm³/g), in a tubular reactor having a length:diameter ratio of 3.4:1. Per hour, 158.5 parts of N-(2-methyl-prop-1-enyl)-formamide are fed into the reactor, which is preheated to 450°–480° C. and kept at 133 mbar. After distillation of the product, 95.9 parts per hour of 3,3-dimethylacrylonitrile (74% of theory, based on N-(2-methyl-prop-1-enyl)-formamide employed), of boiling point 80° C./153 mbar, are obtained. The conversion of starting material III is virtually quantitative.

EXAMPLE 3

(a) (1st step). 1,075 parts of 2-methylbutanal, 450 parts of formamide and 47.5 parts of p-toluenesulfonic acid are introduced into a stirred apparatus equipped with a reflux condenser and water separator, and the mixture is refluxed for 6 hours whilst keeping the internal temperature during the reaction at about 92°–100° C. by adding a further 235 parts of 2-methylbutanal in portions. 107 parts of water are separated off. On subsequent distillation of the reaction mixture, 704 parts of unconverted 2-methylbutanal and 641 parts of N-(2-methyl-but-1-enyl)-formamide, of boiling point 84° C./0.35 mbar, are obtained, the latter corresponding to a yield of 80.5%, based on 2-methylbutanal converted.

(b) (2nd step). The reaction tube (length:diameter = 1.7:1; 50 parts by volume of catalyst) contains a catalyst zone which is only 5.5 cm high. Using a procedure similar to Example 2, 107.1 parts per hour of N-(2-methyl-but-1-enyl)-formamide are reacted at 430° C. and 133 mbar. The conversion of the starting material is virtually complete. 68.6 parts per hour of 3-methyl-pent-2-enonitrile, boiling point 87°–94° C./152 mbar, are obtained, corresponding to a yield of 76.1% of theory, based on N-(2-methyl-but-1-enyl)-formamide employed.

EXAMPLE 4

(a) (1st step). 500 parts of 2-methylpentanal, 180 parts of formamide. 38 parts of p-toluenesulfonic acid and 200 parts by volume of cyclohexane are refluxed for 3½ hours at 98° C. in a stirred apparatus equipped with a reflux condenser and water separator; 68 parts of water are separated off. on subsequent distillation of the reaction mixture, 319 parts of N-(2-methyl-pent-1-enyl)-formamide, boiling point 100°–101° C./0.4 mbar, corresponding to a yield of 68.1 percent based on 2-methylpentanal converted, are obtained in addition to the cyclohexane and to 131 parts of unconverted 2-methylpentanal.

(b) (2nd step). 105.3 parts per hour of N-(2-methyl-pent-1-enyl)-formamide are reacted at 490° C. and 133 mbar by a method similar to that of Example 3. 72.6 parts per hour of 3-methyl-hex-2-enonitrile, boiling point 112°–114° C./153 mbar, are obtained, corresponding to a yield of 80.4 percent, based on N-(2-methyl-pent-1-enyl)-formamide employed.

EXAMPLE 5

(a) (1st step). 768 parts of 2-ethylhexanal, 225 parts of formamide, 24 parts of p-toluenesulfonic acid and 600 parts by volume of cyclohexane are refluxed for 6½ hours at 92°–95° C. in a stirred apparatus equipped with a reflux condenser and water separator; 81 parts of water are separated off. The reaction mixture is subjected to fractional distillation. In addition to 393 parts of unconverted 2-ethylhexanal, 339 parts of N-(2-ethyl-hex-1-enyl)-formamide, boiling point 117° C./0.7 mbar, are obtained, corresponding to a yield of 74.7% of theory, based on 2-ethylhexanal converted.

(b) (2nd step). 51.9 parts per hour of N-(2-ethyl-hex-1-enyl)-formamide are reacted at 410° C. and 67 mbar by a method similar to that of Example 3. 28.2 parts per hour of 3-ethyl-hept-2-enonitrile, boiling point 96° C./33 mbar, are obtained, corresponding to a yield of 77.3% of theory, based on N-(2-ethyl-hex-1-enyl)-formamide employed.

EXAMPLE 6

(a) (1st step). 1,340 parts of 2-phenylpropanal, 450 parts of formamide, 95 parts of p-toluenesulfonic acid and 420 parts by volume of cyclohexane are refluxed for 4½ hours at 95°–98° C. in a stirred apparatus equipped with a reflux condenser and water separator; 144 parts of water are separated off. The reaction mixture is subjected to fractional distillation. The distillate is extracted with 500 parts by volume of ether. Distillation of the ether extract under reduced pressure gives 118 parts of unconverted 2-phenylpropanol, whilst crystallization of the extraction residue and the distillation residue gives 947 parts of N-(2-phenyl-prop-1-enyl)-formamide, corresponding to a yield of 64.5% of theory, based on 2-phenylpropanol converted.

(b) (2nd step). 69 parts per hour of N-(2-phenylprop-1-enyl)-formamide which have been fused at 130° C. are reacted at 500° C. and 0.4 mbar by a method similar to that of Example 3. 44 parts per hour of 3-phenylbut-2-enonitrile, boiling point 90°–91° C./0.5 mbar, are obtained, corresponding to a yield of 71.9% of theory, based on N-(2-phenyl-prop-1-enyl)-formamide employed.

We claim:

1. A process for the preparation of α,β-unsaturated nitriles of the formula

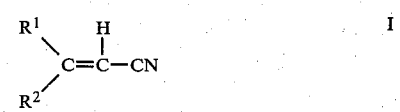

where $R^1$ and $R^2$ may be identical or different and each may be substituted or unsubstituted and each is alkyl of 1 to 7 carbons, cycloalkyl of 5 to 7 carbons, aralkyl or alkylaryl of 7 to 12 carbon atoms, aromatic, or piperidin-2-yl or $R^1$ and $R^2$ together with the adjacent carbon may also be members of a 5- to 6-membered alicyclic ring, and any of $R^1$ and $R^2$ may be substituted by alkyl or alkoxy of one to four carbon atoms, by first reacting, an aldehyde of the formula

where $R^1$ and $R^2$ have the above meanings, at a temperature from 40° to 150° C. with formamide in the presence of a catalytic amount of an inorganic acid, aromatic sulfonic acid and/or halogen-substituted aliphatic carboxylic acid in the absence of an added solvent or in the presence of an organic non-alcoholic and non-aromatic solvent which is inert under the reaction conditions, after which, in a second step, the resulting N-alkenylformamide of the formula

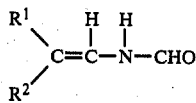

where $R^1$ and $R^2$ have the above meanings, is passed, in the gas phase, over a dehydration catalyst at from 250° to 700° C.

2. A process as set forth in claim 1, wherein the reaction is carried out with from 0.75 to 4 moles of starting material II per mole of formamide.

3. A process as set forth in claim 1, wherein the reaction in the first step is carried out at from 40° to 150° C.

4. A process as set forth in claim 1, wherein the reaction in the first step is carried out at from 60° to 120° C.

5. A process as set forth in claim 1, wherein the reaction in the first step is carried out for from 0.5 to 25 hours.

6. A process as set forth in claim 1, wherein the reaction in the first step is carried out with from 0.1 to 15 equivalents of acid per mole of formamide.

7. A process as set forth in claim 1, wherein the reaction is carried out in the presence of from 10 to 500 percent by weight, based on starting material II, of an organic non-aromatic solvent which is inert under the reaction conditions.

8. A process as set forth in claim 1, wherein the reaction in the second step is carried out at from 250° to 700° C.

9. A process as set forth in claim 1, wherein the reaction in the second step is carried out at from 350° to 500° C.

10. A process as set forth in claim 1, wherein the reaction in the second step is carried out at from 0.1 to 500 mbar.

11. A process as set forth in claim 1, wherein the reaction in the second step is carried out in the presence of from 0.01 to 20 percent by weight, based on starting material III, of a dehydration catalyst.

12. A process as set forth in claim 1, wherein the reaction in the second step is carried out using from 1 to 100 moles of starting material III per hour per liter of catalyst.

13. A process as set forth in claim 1, wherein isobutyraldehyde is first reacted with formamide in the presence of toluenesulfonic acid to form N-(2-methyl-prop-1-enyl)-formamide, after which, in a second step, said N-(2-methyl-prop-1-enyl)-formamide is passed, in the gas phase, over a silica gel catalyst to obtain 3,3-dimethylacrylonitrile.

* * * * *